US006303382B1

(12) United States Patent
Adams et al.

(10) Patent No.: US 6,303,382 B1
(45) Date of Patent: *Oct. 16, 2001

(54) FORMATION OF AND METHODS FOR THE PRODUCTION OF LARGE *BACILLUS THURINGIENSIS* CRYSTALS WITH INCREASED PESTICIDAL ACTIVITY

(76) Inventors: Lee Fremont Adams, 1880 Cowell Blvd., No. 112; Michael David Thomas, 3175 Newport Terrace; Alan P. Sloma, 849 Donovan Ct.; William R. Widner, 894 E. 9th St., Apt. 301, all of Davis, CA (US) 95616

(*) Notice: Subject to any disclaimer, the term of this patent is extended or adjusted under 35 U.S.C. 154(b) by 0 days.

This patent is subject to a terminal disclaimer.

(21) Appl. No.: 08/771,190

(22) Filed: Dec. 20, 1996

Related U.S. Application Data

(60) Division of application No. 08/274,608, filed on Jul. 13, 1994, which is a continuation-in-part of application No. 08/092,338, filed on Jul. 15, 1993, now abandoned.

(51) Int. Cl.$^7$ .................................................. C12N 15/63
(52) U.S. Cl. .......................................... 435/477; 435/485
(58) Field of Search .................................... 435/471, 477, 435/485

(56) References Cited

U.S. PATENT DOCUMENTS 5,955,367 * 9/1999 Adams et al. ........................ 435/485

FOREIGN PATENT DOCUMENTS

| 0127328 | 12/1984 | (EP) . |
| 9109129 | 6/1991 | (WO) . |
| 9425611 | 11/1994 | (WO) . |
| 9502695 | 1/1995 | (WO) . |

OTHER PUBLICATIONS

Albertinei et al., "Amplification of a Chromosomal Region in *Bacillus subtilis*", *Journal of Bacteriology*, 162(3):1203–1211 (1985).
Arantes, et al., "Construction of cloning vectors for *Bacillus thuringiensis*", *Gene*, 108:115–119 (1991).
Gawron–Burke, et al., "Genetic Manipulation of *Bacillus thruingiensis* Insecticidal Cyrstal Protein Genes in Bacteria", *Genetic Engineering*, 13:237–263 (1991).

Baum, et al., "Novel Cloning Vectors for *Bacillus thuringiensis*", *Applied and Environmental Microbiology*, 56(11):3420–3428 (1990).
Calogero, et al., "Expression of a Cloned *Bacillus thuringiensis* Delta–Endotoxin Gene in *Bacillus subtilis*", *Applied and Environmental Microbiology*, 55(2):446–453 (1989).
Gamel, et al., "Characterization and properties of a novel plasmid vector for *Bacillus thuringiensis* displaying compatibility with host plasmids", *Gene*, 1:17–26 (1992).
Höfte, et al., "Insecticidal Crystal Proteins of *Bacillus thuringiensis*", *Microbiological Reviews*, 53(2):242–255 (1989).
Jorgensen, et al., "In vivo genetic engineering: homologous recombination as a tool for plasmid construction", *Gene*, 96:37–41 (1990).
van der Laan, et al., "Cloning, Characterization, and Multiple Chromosomal Integration of a Bacillus Alkaline Protease Gene", *American Society for Microbiology*, 901–909 (1991).
Lereclus, et al., "Expansion of Insecticidal Host Range of *Bacillus thuringiensis* by in Vivo Genetic Recombination", *Bio/Technology*, 10:418–421 (1992).
Lereclus, et al., "Transformation and expression of a cloned δ–endotoxin gene in *Bacillus thuringiensis*", *FEMS Microbiology Letters*, 60:211–217 (1989).
Mori, et al., "Designed Gene Amplification of the *Bacillus subtilis* Chromosome", *Journal of General Microbiology*, 134:85–95 (1988).
Schurter, et al., "Efficient transformation of *Bacillus thuringiensis* and *B. cereus* via electroporation: Transformation of acrystalliferous strains with a cloned delta–endotoxin gene", *Mol Gen Genet*, 218:177–181 (1989).
Young, M., "Gene Amplification in *Bacillus subtilis*", *Journal of General Microbiology*, 130:1613–1621 (1984).

* cited by examiner

Primary Examiner—Robert A. Schwartzman

(57) ABSTRACT

The invention relates to a method for producing an integrant(s) of *Bacillus thuringiensis* which produces a larger quantity of a crystal delta-endotoxin with greater pesticidal activity as compared to the crystal delta-endotoxin produced by the corresponding parental strain. The crystal delta-endotoxin produced by the integrant *Bacillus thuringiensis* will have an activity directed towards the same pest(s) as its parent *Bacillus thuringiensis* crystal delta-endotoxin. The invention further relates to such integrants, compositions comprising such integrants, as well as methods for controlling a pest(s) using these compositions.

24 Claims, 5 Drawing Sheets

FORMATION OF AND METHODS FOR THE PRODUCTION OF LARGE *BACILLUS THURINGIENSIS* CRYSTALS WITH INCREASED PESTICIDAL ACTIVITY

This application is a divisional of U.S. patent application Ser. No. 08/274,608, filed Jul. 13, 1994, which is a continuation-in-part of U.S. patent application Ser. No. 08/092,338, filed Jul. 15, 1993, now abandoned.

FIELD OF THE INVENTION

The invention relates to methods for obtaining an integrant(s) of *Bacillus thuringiensis* which produces a larger quantity of a crystal delta-endotoxin with greater pesticidal activity and optionally a larger crystal size as compared to a corresponding parental strain. The crystal delta-endotoxin produced by the integrant of *Bacillus thuringiensis* will have activity directed to the same pest(s) as its parental *Bacillus thuringiensis* crystal delta-endotoxin. The invention further relates to such integrant(s), spores or crystal delta-endotoxins thereof, compositions comprising such integrant(s), as well as methods for controlling a pest(s) using these compositions.

BACKGROUND OF THE INVENTION

Every year, pests detrimental to agriculture, forestry, and public health cause losses in the millions of dollars. Various strategies have been used in attempting to control such pests.

One strategy is the use of chemical pesticides with a broad range or spectrum of activity. However, there are a number of disadvantages to using such chemical pesticides. Specifically, because of their broad spectrum of activity, these pesticides may destroy non-target organisms such as beneficial insects and parasites of destructive pests. Additionally, chemical pesticides are frequently toxic to animals and humans. Furthermore, targeted pests frequently develop resistance when repeatedly exposed to such substances.

Another strategy has involved the use of biopesticides, which make use of naturally occurring pathogens to control insect, fungal and weed infestations of crops. An example of a biopesticide is a bacterium which produces a substance toxic to the infesting pest A biopesticide is generally less harmful to non-target organisms and the environment as a whole than chemical pesticides.

The most widely used biopesticide is *Bacillus thuringiensis*. *Bacillus thuringiensis* is a motile, rod-shaped, gram-positive bacterium that is widely distributed in nature, especially in soil and insect-rich environments. During sporulation, *Bacillus thuringiensis* produces a paraspora crystal inclusion(s) which is insecticidal upon ingestion to susceptible insect larvae of the orders Lepidoptera, Diptera, and Coleoptera. The inclusion(s) may vary in shape, number, and composition. They are comprised of one or more proteins called delta-endotoxins, which may range in size from 27–140 kDa. The insecticidal delta-endotoxins are generally converted by proteases in the larval gut into smaller (truncated) toxic polypeptides, causing midgut destruction, and ultimately, death of the insect (Höfte and Whiteley, 1989, *Microbiol. Rev.* 53:242–255).

There are several *Bacillus thuringiensis* strains that are widely used as biopesticides in the forestry, agricultural, and public health areas. *Bacillus thuringiensis* subsp. *kurstaki* and *Bacillus thuringiensis* subsp. *aizawai* have been found to produce delta-endotoxins specific for Lepidoptera. *Bacillus thuringiensis* subsp. *israelensis* has been found to produce delta-endotoxins specific for Diptera (Goldberg, 1979, U.S. Pat. No. 4,166,112). *Bacillus thuringiensis* subsp. *tenebrionis* (Krieg et al., 1988, U.S. Pat. No. 4,766,203), has been found to produce a delta-endotoxin specific for Coleoptera.

*Bacillus thuringiensis* subsp. *tenebrionis* has been deposited with the German Collection of Microorganisms under accession number DSM 2803. *Bacillus thuringiensis* subsp. *tenebrionis* was isolated in 1982 from a dead pupa of the mealworm *Tenebrio molitor* (Tenebrionidae, Coleoptera). The strain produces within each cell one spore and one or more pesticidal parasporal crystals which are of flat platelike form with an edge length of about 0.8 μm to 1.5 μm. It belongs to serotype H8a,8b and pathotype C of *Bacillus thuringiensis* (Krieg et al., 1987, *System. Appl. Microbiol.* 9, 138–141; Krieg et al., 1988, U.S. Pat. No. 4,766,203). It is only toxic against certain leaf-eating beetle larvae (Chrysomelidae), but ineffective against caterpillars (Lepidoptera), mosquitoes (Diptera) or other insects.

The isolation of another coleopteran toxic *Bacillus thuringiensis* strain was reported in 1986 (Herrnstadt et al., 1986, *Bio/Technology* 4:305–308; Hermstadt and Soares, 1988, U.S. Pat. No. 4,764,372). This strain, designated "*Bacillus thuringiensis* subsp. *san diego*", M-7, has been deposited at the Northern Regional Research Laboratory, USA under accession number NRRL B-15939. However, the assignee of the '372 patent, Mycogen, Corp. has publicly acknowledged that *Bacillus thuringiensis* subsp. *san diego* is *Bacillus thuringiensis* subsp. *tenebrionis*. Furthermore, the '372 patent has been assigned to Novo Nordisk A/S. A spo-cry+ (asporogenous crystal forming) mutant of M-7 has purportedly been obtained by culturing M-7 in the presence of ethidium bromide (Hermstadt and Gaertner, 1987, EP Application No. 228,228). However, there was no indication of increased production of delta-endotoxin, increased parasporal crystal size, and/or increased pesticidal activity relative to the parental, M-7 strain.

The crystal proteins are encoded by cry (crystal protein) genes. The cry genes have been divided into six classes and several subclasses based on relative amino acid homology and pesticidal specificity. The six major classes are Lepidoptera-specific (cryI), Lepidoptera- and Diptera-specific (cryII), Coleoptera-specific (cryIII), Diptera-specific (cryIV) (Höfte and Whiteley, 1989, *Microbiol. Rev.* 53:242–255), Coleoptera- and Lepidoptera-specific (referred to as cryV genes by Tailor et al., 1992, *Mol. Microbiol.* 6:1211–1217); and Nematode-specific (referred to as cryV and cryVI genes by Feitelson et al., 1992, *Bio/Technology* 10:271–275).

Delta-endotoxins have been produced by recombinant DNA methods. The delta-endotoxins produced by recombinant DNA methods may or may not be in crystal form. Various cry genes have been cloned, sequenced, and expressed in various hosts, e.g., *E. coli* (Schnepf et al., 1987, *J. Bacteriol.* 169:4110–4118), *Bacillus subtilis* (Shivakumar et al., 1986, *J. Bacteriol.* 166:194–204), and maize plants (Koziel et al., 1993, Bio/Technology 11:194–200).

Amplification of cry genes has been achieved in *Bacillus subtilis*. The delta-endotoxin gene of *Bacillus thuringiensis* subsp. *kurstaki* HD73 has been cloned into *Bacillus subtilis* using an integrative plasmid and amplified (Calogero et al., 1989, *Appl. Environ. Microbiol.* 55:446–453). However, no increase in crystal size was observed as compared to *Bacillus thuringiensis* subsp. *kurstaki* HD73. Furthermore, no difference in pesticidal activity was reported.

The level of expression of delta-endotoxin genes appears to be dependent on the host cell used (Skivakumar et al., 1989, Gene 79:21–31). For example, Skivakumar et al. found significant differences in the expression of the cryIA and cryIIA delta-endotoxin genes of *Bacillus thuringiensis* subsp. *kurstaki* in *Bacillus subtilis* and *Bacillus megaterium*. The cryIA gene was expressed when present on a multicopy vector in *Bacillus megaterium*, but not in *Bacillus subtilis*. The cryIIA gene was expressed in both hosts, but at a higher level in *Bacillus megaterium*. Sections of *Bacillus megaterium* cells expressing these delta-endotoxin genes were examined by electron microscopy; the presence of large bipyramidal crystals in these cells was detected. However, there is no indication that these crystals are any larger than crystals found in *Bacillus thuringiensis* subsp. *kurstaki* which normally contain these genes. Results from bioassays of the *Bacillus megaterium* cells expressing these delta-endotoxin genes indicate that there was no increase in pesticidal activity as compared to *Bacillus thuringiensis* subsp. *kurstaki*. Indeed, five times the concentration of *Bacillus megaterium* than *Bacillus thuringiensis* subsp. *kurstaki* was required to obtain the same insect killing effect.

Recombinant *Bacillus thuringiensis* strains have also been disclosed. Shuttle vectors with various copy numbers containing the cryIIIA gene, which encodes a delta-endotoxin protein specific for pests of the order Coleoptera, were constructed and transformed into *Bacillus thuringiensis* subsp. *kurstaki* HD1 Cry-B (Arantes and Lereclus, 1991, *Gene* 108:115–119). It was found that when the gene expression level and vector copy number were compared, a plateau in delta-endotoxin production was reached with a copy number of about fifteen per equivalent chromosome. The crystal size and pesticidal activity of these recombinants were not determined or disclosed in that reference.

Lecadet et al. (1992, *Appl. Environ. Microbiol* 58:840–849) and Lereclus et al. (1992, *Bio/Technology* 10:418–421) disclose the construction of various recombinant *Bacillus thuringiensis* strains expressing the cryIA(a) and/or the cryIIIA genes. Those strains with dual specificities possessed pesticidal activity corresponding to those of the parental strains. In one instance, the cryIIIA gene was introduced via transduction into a heterologous cry-strain. In this instance, the pesticidal activity was increased relative to *Bacillus thuringiensis* subsp. *tenebrionis*; a larger crystal was also observed (Lecadet et al., 1992, *Appl. Environ. Microbiol.* 58:840–849). Lecadet et al. attributed the hyperexpression of the CryIIIA protein to the release of the cryIIIA gene from negative regulation in the heterologous strain.

The utility of *Bacillus thuringiensis* strains for the control of pests of the orders Lepidoptera, Diptera, and Coleoptera is dependent upon efficient and economical production of the crystal delta-endotoxin(s) and the potency of the product produced. This, in turn, is dependent upon the amount of crystal delta-endotoxin(s) which can be produced by fermentation of the *Bacillus thuringiensis* strains.

*Bacillus thuringiensis* has been used for many years for the production of pesticides. Mutants of *Bacillus thuringiensis* have also been disclosed. Generally, such mutants have been obtained using classical mutagenesis. There has been disclosed, for example, a mutant of *Bacillus thuringiensis* subsp. *tenebrionis* which produces a crystal delta-endotoxin with a larger crystal size and greater pesticidal activity as compared to a corresponding parental strain (Gurtler and Petersen, 1994, U.S. Pat. No. 5,279,962).

Mutants producing crystal delta-endotoxins with a larger crystal size and increased pesticidal activity would give a more efficient and economical production of *Bacillus thuringiensis* crystal delta-endotoxin(s), and a possibility for manufacture of *Bacillus thuringiensis* products with increased potency at equal or lower cost. This, in turn, would be an advantage for the user as reduced volumes of pesticide formulation have to be stored and handled for a given acreage. In addition, the users will have less container material to dispose of, thereby, reducing the impact on the environment.

For example, in controlling beetle larvae, *Bacillus thuringiensis* subsp. *tenebrionis* crystal delta-endotoxin preparations have been of relatively low potency or strength requiring the application of relatively large amounts of the preparations to areas to be treated, such as 5 to 10 liter/ha compared to 1 to 2 liter/ha of most other *Bacillus thuringiensis* products and most other insecticides. It is advantageous to obtain products with increased pesticidal activity. Consequently, a recognized need for products of improved strength exists.

One way to fulfill this need is to concentrate the preparations. However, concentration adds considerably to the production cost in comparison to the savings obtained in storage and transportation. And, in some cases, concentration to obtain a pesticidally acceptable level is not achievable or practical.

A more expedient solution would be to create integrants of existing *Bacillus thuringiensis* strains which produce substantially larger quantities of crystal delta-endotoxin with greater pesticidal activity compared to wild-type strains.

The art has strived to improve the effectiveness and to broaden the host range of *Bacillus thuringiensis*. Means have included isolating *Bacillus thuringiensis* strains with new or improved toxicity, engineering present *Bacillus thuringiensis* strains, and designing more effective formulations by combining *Bacillus thuringiensis* crystal delta-endotoxins and spores with new pesticidal carriers or with chemical pesticides.

SUMMARY OF THE INVENTION

The present invention relates to methods for obtaining an integrant of *Bacillus thuringiensis* which produces a larger quantity of a crystal delta-endotoxin with greater pesticidal activity and optionally a larger crystal size as a result of gene amplification or hyperexpression as compared to the corresponding parental strain, wherein the integrant of *Bacillus thuringiensis* will have an activity directed towards the same pest as the corresponding parental strain crystal delta-endotoxin.

In one embodiment, the integrant is obtained by
 (a) introducing into a cell of a parental strain a DNA construct lacking a *Bacillus thuringiensis* origin of replication comprising (i) a DNA sequence encoding a delta-endotoxin, wherein said delta-endotoxin is the same delta-endotoxin as the parental strain delta-endotoxin; (ii) a DNA sequence which is homologous with a region of the genome of said cell or said delta-endotoxin; and (iii) a selectable marker, to obtain an integrated cell;
 (b) integrating the introduced DNA construct of step (a) into the genome of said parental strain by homologous recombination in the presence of a selecting agent to obtain an integrant; and
 (c) selecting said integrant from the culture of step (b).
In another embodiment, the integrant is obtained by
 (a) introducing into a cell of a parental strain (i) a first DNA vector comprising a first origin of replication and at least one functional gene encoding at least one factor required for plasmid replication from said first origin of replication, and with (ii) a second DNA vector comprising a second origin of replication but lacking a functional gene encoding a factor required for plasmid replication from the second origin of replication, as well as a DNA sequence encoding a *Bacillus thuringiensis* delta-endotoxin, a DNA sequence that is homologous with a region of the genome of said parental strain, and a selectable marker and (b) culturing the cell of step (a) under selective conditions leading to the loss of the first DNA vector and integration of said second DNA vector into the genome of said parental cell by homologous recombination.

The invention further relates to said integrant, or spore thereof. The invention also relates to a pesticidal composition comprising such an integrant, or spore or crystal delta-endotoxin thereof, and a pesticidally acceptable carrier as well as methods for controlling a pest(s) using such a composition.

The invention also relates to a DNA construct lacking a *Bacillus thuringiensis* origin of replication comprising (i) a DNA sequence encoding a delta-endotoxin, wherein said DNA sequence is obtained from a *Bacillus thuringiensis* strain; (ii) a DNA sequence that is homologous with a region of the genome of said parental strain or said delta-endotoxin; and (iii) a selectable marker as well as a recombinant DNA vector comprising the construct.

DEFINITIONS

"Integrant" as defined herein is a *Bacillus thuringiensis* strain containing an additional DNA segment (generally, a cry gene, antibiotic resistance gene, and plasmid-associated DNA) inserted into the genome of said strain by homologous recombination.

A "genome" as defined herein is all DNA, both chromosomal and plasmid, within a *Bacillus thuringiensis* cell.

"Greater pesticidal activity" as defined herein means at least 1.5 times more activity against a pest, through killing or stunting of the growth of the pest, than the corresponding parental strain. In a preferred embodiment, the pesticidal activity of the integrant is between about 1.5 to about 10 times greater than the pesticidal activity of the corresponding parental *Bacillus thuringiensis* strain.

"Larger quantity" as defined herein means that the integrant produces at least 1.5 times the amount of a crystal delta-endotoxin as the parental strain.

"Larger crystal size" as defined herein means that the largest face of the crystal of the integrant has at least 1.2 times the surface area or volume of the crystal of the parental strain.

DETAILED DESCRIPTION OF THE INVENTION

The invention relates to a method(s) for obtaining an integrant(s) of *Bacillus thuringiensis* which produces a larger quantity of crystal delta-endotoxin with a greater pesticidal activity and optionally a larger crystal size as compared to the crystal delta-endotoxin produced by the correspond parental strain.

The invention further relates to the integrant(s). The crystal delta-endotoxin produced by the integrant of *Bacillus thuringiensis* will have an activity directed towards the same pest(s) as the crystal delta-endotoxin produced by the corresponding parental *Bacillus thuringiensis* including, but not limited to, *Bacillus thuringiensis* subsp. *kurstaki*, *Bacillus thuringiensis* subsp. *aizawai*, *Bacillus thuringiensis* subsp. *galleriae*, *Bacillus thuringiensis* subsp. *entomocidus*, *Bacillus thuringiensis* subsp. *tenebrionis*, *Bacillus thuringiensis* subsp. *thuringiensis*, *Bacillus thuringiensis* subsp. *alesti*, *Bacillus thuringiensis* subsp. *canadiensis*, *Bacillus thuringiensis* subsp. *darmstadiensis*, *Bacillus thuringiensis* subsp. *dendrolimus*, *Bacillus thuringiensis* subsp. *finitimus*, *Bacillus thuringiensis* subsp. *kenyae*, *Bacillus thuringiensis* subsp. *morrisoni*, *Bacillus thuringiensis* subsp. *subtoxicus*, *Bacillus thuringiensis* subsp. *toumanoffi*, and *Bacillus thuringiensis* subsp. *israelensis*. The pest may be, for example, an insect, snail, mite or nematode. In a most specific embodiment, the integrant has all of the identifying characteristics of strains EMCC0082, deposited with the NRRL and having the accession number NRRL B-21106; EMCC0083, deposited with the NRRL and having the accession number NRRL B-21107; EMCC0115, deposited with the NRRL and having the accession number NRRL B-21286; and EMCC0116, deposited with the NRRL and having the accession number NRRL B-21287.

The invention further relates to compositions comprising such an integrant(s) as well as methods for controlling a pest(s) using these compositions.

Methods for Obtaining Integrants

In one embodiment, the integrant of the present invention may be obtained by (a) introducing into a cell of a parental *Bacillus thuringiensis* strain a DNA construct lacking a *Bacillus thuringiensis* origin of replication comprising (i) a DNA sequence encoding a delta-endotoxin, wherein said delta-endotoxin is the same delta-endotoxin as the parental strain delta-endotoxin; (ii) a DNA sequence which is homologous with a region of the genome of said cell which can be the said delta-endotoxin itself, and (iii) a selectable marker; (b) integrating the introduced DNA construct into the genome by homologous recombination; (c) amplifying the integrated DNA sequence by culturing the integrant of step (b) in the presence of increasing amounts of an agent that selects for the selectable marker; and (d) selecting said amplified strain from the culture of the integrant of step (c).

Figure 1:
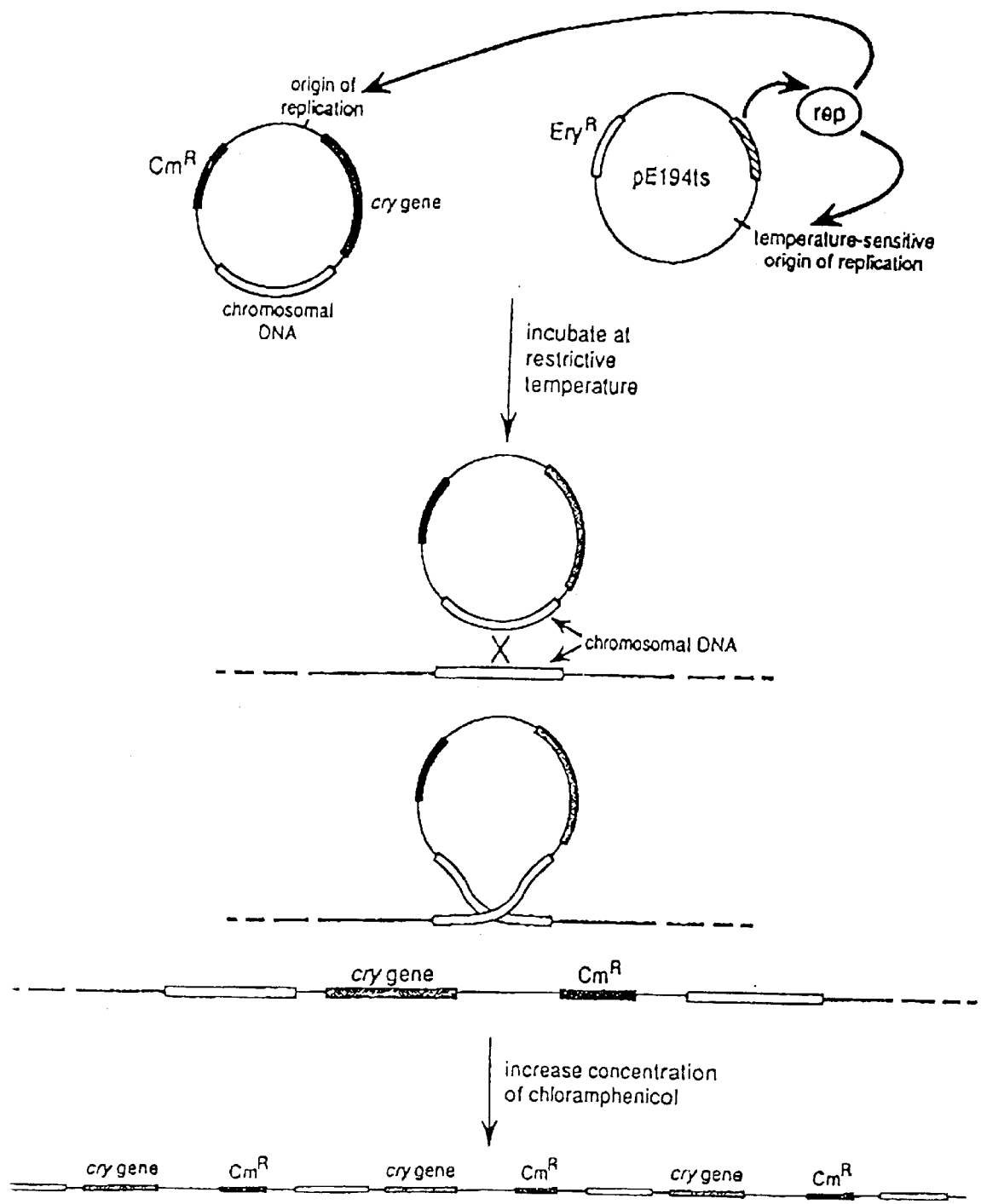
FIG. 1 shows a diagram of the "two-plasmid" integration system.

In another embodiment, the integrant of the present invention can be obtained by the "two-plasmid" integration system developed by Jørgenser et al. (Patent Application No. WO 91/09129, see FIG. 1). This system relies on a first or helper plasmid, which comprises an origin of replication and at least one functional gene encoding at least one factor requiried for plasmid replication, e.g., temperature sensitive replication proteins which function in trans, and a second vector or an integrative plasmid, which cannot replicate in the absence of the helper plasmid. The integrative plasmid of the present invention comprises (i) a cry gene, (ii) a region of homology with the host genome (for example, the 16S rRNA gene or the phospholipase C gene or cry gene itself), and (iii) a selectable marker. The first plasmid may also comprise a DNA sequence which encodes a selectable marker, e.g., an antibiotic resistance marker which differs from that encoded by the helper plasmid. The helper plasmid may be added before or simultaneously with the integrative plasmid.

In a specific embodiment, the helper plasmid is introduced, by electroporation, into the desired host, such as *Bacillus thuringiensis* subsp. *tenebrionis* strain NB125, and maintained by the addition of a selection agent, for example, an antibiotic such as erythromycin, at a temperature which permits proper functioning of the temperature sensitive Rep protein (e.g., 30° C.). Then, the integrative plasmid lacking a functional replication protein (e.g., Rep protein) is introduced into the same host strain, and maintained by selection with a selecting agent, e.g., chloramphenicol. Selection with chloramphenicol alone is sufficient to maintain both plasmids because the integrative plasmid cannot exist without the helper plasmid. Growth at a higher temperature, e.g., 37° C., does not permit replication of the helper plasmid. In the absence of the helper plasmid, the integrative plasmid, encoding chloramphenicol resistance, also cannot replicate. Therefore, the only way that the host cell can maintain resistance to chloramphenicol is by integration of the integrative plasmid by a Campbell recombination event at the region of homology that it shares with the *Bacillus thuringiensis* genome. Consequently, the DNA is integrated into the genome of the host strain.

In a preferred embodiment, the DNA sequence encodes the same delta-endotoxin as the delta-endotoxin produced by the parental *Bacillus thuringiensis* strain. The "parental strain" as defined herein is the original *Bacillus thuringiensis* strain before introduction, integration, and amplification of a DNA construct. The parental strain may be a wild-type *Bacillus thuringiensis* strain from which the plasmid encoding the cry gene has been cured.

The DNA sequence encoding a delta-endotoxin may be selected from the group including, but not limited to, a cryI, cryII, cryIII, cryIV, cryV, or cryVI gene. In one embodiment, the DNA sequence encoding a delta-endotoxin comprises the cryIIIA gene. The cryIIIA gene encodes a delta-endotoxin specific for coleopteran pests. The DNA sequence comprising the cryIIIA gene may be obtained from a strain of *Bacillus thuringiensis* subsp. *tenebrionis*. For example, the cryIIIA DNA sequence is obtained from NB125 (*Bacillus thuringiensis* subsp. *tenebrionis*) disclosed in PCT Application No. PCT/DK90/00294 and U.S. Pat. No. 5,279,962 and deposited with the Deutsche Sammlung von Mikroorganismen und Zelikylturen GmbH, Mascheroderweg 1b, D-3300 Braunschweig, Federal Republic of Germany on Sep. 14, 1989 with a designation of DSM 5526 and produces the CryIIIA protein. The DNA sequence may also be obtained from NB176, a gamma-irradiation-induced mutant of NB125 that overproduces the CryIIIA protein, disclosed in PCT Application No. PCT/DK90/00294 and U.S. Pat. No. 5,279,962, incorporated herein by reference, and deposited with the Deutsche Sammlung von Mikroorganismen und Zefllulturen GmbH, Mascheroderweg 1b, D-3300 Braunschweig, Pederal Republic of Germany on Aug. 10, 1989 with a designation of DSM 5480. Alternatively, the DNA sequence comprises tie cryIC gene. The cryIC gene encodes a delta-endotoxin specific for lepidopteran pests. The DNA sequence comprising the cryIC gene may be obtained from a strain of *Bacillus thuringiensis* subsp. *aizawai*. In a most specific embodiment, the cryIC DNA sequence is obtained from *Bacillus thuringiensis* subsp. *aizawai* strain EMCC0087.

The vectors or DNA constructs may be introduced into the parental strain by procedures known in the art, e.g., electroporation, protoplasting of cells, transduction, chemical transformation, and regeneration (Macaluso and Mettus, 1991, *J. Bacteriol.* 173:1353–1356; Crawford et al., 1987, *J. Bacteriol.* 169:5423–5428; and Battisti et al., 1985, *J. Bacteriol.* 162:543–550). The DNA construct or vector is integrated by selection into the genome of the parental strain by recombination with a homologous region of the genome of the parental strain. The strain, which in its genome carries the integrated DNA construct, is grown in a medium with increasing amounts of an agent that selects for the selectable marker, e.g., media containing an antibiotic, thereby amplifying the selectable marker and, necessarily, the cry gene as well (Albertni and Galizzi, 1985, *J. Bacteriol.* 162:1203–1211).

In a preferred embodiment, the DNA encoding the delta-endotoxin is amplified in the integrant. In a specific embodiment, such amplification occurs by transferring the integrant to medium comprising greater amounts of an agent that selects for the selectable marker. This step may be repeated several times with increasing amounts of the agent selecting for the selectable marker.

In yet another embodiment, additional copies of sigma factor genes, e.g., those encoding sigma 35 and sigma 28 proteins (Adams et al., 1991, *J. Bacteriol.* 173:3846–3854) may be inserted into a parental *Bacillus thuringiensis* strain and amplified by means described, supra, in order to overproduce the delta-endotoxin encoded by a cry gene. Those sigma factors bind to RNA polymerase and direct transcription of cry gene promoters. The genes encoding sigma factors may be introduced into the parental strain by procedures described, supra.

In another embodiment, the promoter region of a cry gene may be mutagenized to achieve "up" mutations that lead to delta-endotoxin overexpression. The mutagenized gene may then be inserted, and amplified, if necessary, by means disclosed, supra. Alternatively, other regulatory factors that control and/or limit cry gene expression such as the sporulation inhibitor gene (sin) may be mutagenized (Dubnau, 1993, Genetic Exchange, p. 570, in A. L. Sonenshein (ed.), *Bacillus subtilis and Other Gram-Positive Bacteria,* American Society for Microbiology, Washington, D.C.)

In another embodiment, multiple promoters may be inserted upstream of a cloned cry gene, and then inserted into the parental *Bacillus thuringiensis* strain by means disclosed, supra, in order to overproduce the delta-endotoxin encoded by a cry gene.

The integrant of the present invention may be cultured using media and fermentation techniques known in the art (see, for example, Rogoff et al., 1969, *J. Invertebrate Path.* 14:122–129; Dulmage et al., 1971, *J. Invertebrate Path.* 18:353–358; Dulmage et al., in *Microbial Control of Pests and Plant Diseases,* H. D. Burges (ed.), Academic Press, New York, 1980). Upon completion of the fermentation cycle, the *Bacillus thuringiensis* crystal delta-endotoxin(s) and spores can be harvested from the fermentation broth by means well known in the art, e.g., centrifugation.

Purification of the crystal delta-endotoxins and/or delta-endotoxin proteins or spores of the integrant strain of the present invention can be carried out by various procedures known in the art including, but not limited to, ultrafiltration, differential extraction, density gradient centrifugation, chromatography, or other techniques for protein and/or particle purification.

The activity of the crystal delta-endotoxin or spores of the integrant strain of the present invention against various pests may be bioassayed using procedures known in the art, such as artificial diet incorporation, artificial diet overlay, leaf painting, leaf dip, foliar spray, and aquatic assay.

Compositions

The integrant *Bacillus thuringiensis* strains and/or spores of the invention, can be formulated into a pesticidal composition(s), that is for example, a suspension, a dispersion, an aqueous emulsion, a dusting powder, a dispersible powder, an emulsifiable concentrate, an aerosol or micro or macroencapulated granules or any other formulation that gives controlled release of Bacillus thuringiensis. Such compositions may be obtained by the addition of a surface active agent, e.g., a dispersing agent, emulsifying agent or wetting agent, or an inert carrier or other component to facilitate handling and application for particular target pests.

Suitable surface-active agents include anionic compounds such as a carboxylate, for example, a metal carboxylate of a long chain fatty acid; a N-acylsarcosinate; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl-naphthalene sulphonate; salts or sulphonated naphthalene-formaldehyde condensates or salts of polyacrylic acid; salts of sulphonated phenol-formaldehyde condensates; or more complex sulphonates such as the amide sulphonates, e.g., the sulphonated condensation product of oleic acid and N-methyl taurine or the dialkyl sulphosuccinates, e.g., the sodium sulphonate or dioctyl succinate. Non-ionic agents include condensation products of fatty acid esters, fatty alcohols, fatty acid amides or fatty-alkyl- or alkenyl-substituted phenols with ethylene oxide and/or propylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine as an acetate, naphthenate or oleate; an oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include inorganic minerals such as phyllosilicates, carbonates, sulfates, phosphates; organic materials such as sugar, starches, or cyclodextrins; or botanical materials such as powdered corncobs, rice hulls, walnut shells, cornmeal, pelleted grains, and cellulosic fibers.

The compositions of the present invention can be in a suitable form for direct application or as a concentrate or primary composition which requires dilution with a suitable quantity of water or other diluent before application. The pesticidal concentration will vary depending upon the nature of the particular formulation, specifically, whether it is a concentrate or to be used directly. The composition contains 0.1% to 99%, preferably 0.1% to 95% of the integrant, mutant or variant of the present invention, 1 to 98% of a solid or liquid inert carrier, and 0 to 50%, preferably 0.1% to 50% of a surfactant. These compositions will be administered at about 0.01 lb–5.0 lb per acre when in dry form and at about 0.01 pt–10 pts per acre when in liquid form.

In a further embodiment, the integrants of the present invention can be treated prior to formulation to prolong the pesticidal activity when the cells are applied to the environment of a target pest. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropranol and ethanol; histological fixatives, such as Bouin's fixative and Helly's fixative (see, for example, Humason, Animal Tissue Techniques, W.H. Freeman and Co., 1967); preservatives; UV sunscreens; spray adjuvants (humectants); antifoams; and stickers.

The compositions of the invention can be applied directly to the plant by, for example, spraying or dusting at the time when the pest has begun to appear on the plant or before the appearance of pests as a protective measure. Plants to be protected within the scope of the present invention include, but are not limited to, cereals (wheat, barley, rye, oats, rice, sorghum and related crops), beet (sugar beet and fodder beet), drupes, pomes and soft fruit (apples, pears, plums, peaches, almonds, cherries, strawberries, raspberries, and blackberries, tomatoes), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages and other brassicae, carrots, onions, potatoes, paprika), lauraceae (avocados, cinnamon, camphor), deciduous trees and conifers (lindentrees, yew-trees, oak-trees, alders, poplars, birch-trees, firs, larches, pines), or plants such as maize, tobacco, nuts, coffee, sugar cane, tea, vines hops, bananas and natural rubber plants, as well as ornamentals. The preferred mode of application is by foliar spraying. It is generally important to obtain good control of pests in the early stages of plant growth as this is the time when the plant can be most severely damaged. The spray or dust can conveniently contain another insecticide or pesticide, e.g., fungicide, grass herbicide or fertilizer, if this is thought necessary. In a preferred embodiment, the composition of the invention is applied directly to the plant.

The compositions of the present invention may be effective against pests of the order Coleoptera, e.g., Leptinotarsa sp., *Acanthoscelides obtectus, Callosobruchus chinensis, Epilachna varivestis, Pyrrhalta luteola, Cylas formicarius elegantulus, Listronotus oregonensis,* Sitophilus sp., *Cyclocephala borealis, Cyclocephala immaculata, Macrodactylus subspinosus, Popillia japonica, Rhizotrogus majalis, Alphitobius diaperinus, Palorus ratzeburgi, Tenebrio molitor, Tenebrio obscurus, Tribolium castaneum, Tribolium confusum, Tribolius destructor.* The compositions of the invention may also be effective against insect pests of the order Lepidoptera, e.g., *Achroia grisella, Acleris gloverana, Acleris variana, Adoxophyes orana, Agrotis epsilon, Alabama argillacea, Alsophila pometaria, Amyelois transitella, Anagasta kuehniella, Anarsia lineatella, Anisota senatoria, Antheraea pernyi, Anticarsia gemmatalis,* Archips sp., Argyrotaenia sp., *Athetis mindara, Bombyx mori, Bucculatrix thurberiella, Cadra cautella,* Choristoneura sp., *Cochylis hospes, Colias eurytheme, Corcyra cephalonica, Cydia latiferreanus, Cydia pomonella, Datana integerrima, Dendrolimus sibericus, Desmia funeralis, Diaphania hyalinata, Diaphania nitidalis, Diatraea grandiosella, Diatraea saccharalis, Ennomos subsignaria, Eorewma loftini, Ephestia elutella, Erannis tiliaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americano, Helicoverpa subflexa, Helicoverpa zea, Heliothis virescens,*

Hemileuca oliviae, Homoeosoma electellum, Hyphantria cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrsisalis, Malacosoma sp., Mamestra brassicae, Mamestra configurata, Manduca quinquemaculata, Mandica sexta, Maruca testulalis, Melanchra picta, Operophtera brunmata, Orgyia sp., Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota sultana, Platyptilia carduidactyla, Plodia interpunctella, Plutella xylostella, Pontia protodice, Pseudaletia unipuncta, Pseudoplusia includens, Sabulodes aegrotata, Schizura concinna, Sitotroga cerealella, Spilonota ocellana, Spodoptera sp., Syngrapha falcifera, Thaurnstopoea pityocampa, Tineola bisselliella, Trichoplusia ni, Udea rubigalis, Xylomyges curialis, Yponomeuta padella; Diptera, e.g., Aedes sp., Andes vittatus, Anastrepha ludens, Anastrepha suspensa, Anopheles barberi, Anopheles quadrimaculatus, Armigeres subalbatus, Calliphora stygian, Calliphora vicina, Ceratitis capitata, Chironomus tentans, Chrysomya rufifacies, Cochliomyia macellaria, Culex sp., Culiseta inornata, Dacus oleae, Delia antiqua, Delia platura, Delia radicum, Drosophila melanogaster, Eupeodes corollae, Glossina austeni, Glossina brevipalpis, Glossina fuscipes, Glossina morsitans centralis, Glossina morsitans morsitans, Glossina morsitans submorsitans, Glossina pallidipes, Glossina palpalis gambiensis, Glossina palpalis palpalis, Glossina tachinoides, Haemagogus equinus, Haematobia irritans, Hypoderma bovis, Hypoderma lineatum, Leucopis ninae, Lucilia cuprina, Lucilia sericata, Lutzomyia longlpaipis, Lutzomyia shannoni, Lycoriella mali, Mayetiola destructor, Musca autumnalis, Musca domestica, Neobellieria sp., Nephrotoma suturalis, Ophyra aenescens, PhaenicIa sericata, Phlebotomus sp., Phormia regina, Sabethes cyaneus, Sarcophaga bullata, Scatophaga stercorarIa, Stomaxys calcitrans, Toxorhynchites amboinensis, Tripteroides bambusa; Acari, e.g., Oligonychus pratensis, Panonychus ulmi, Tetranychus urticae; Hymenoptera, e.g., Iridomyrmex humilis, Solenopsis invicta; Isoptera, e.g., Reticulitermes hesperus, Reticulitermes flavipes, Coptotermes formosanus, Zootermopsis angusticollis, Neotermes connexus, Incisitermes minor, Incisitermes immigrans; Siphonaptera, e.g., Ceratophyllus gallinae, Ceratophyllus niger, Nosopsyllus fasciatus, Leptopsylla segnis, Ctenocephalides canis, Ctenocephalides felis, Echicnophaga gallinacea, Pulex irritans, Xenopsylla cheopis, Xenopsylla vexabilis, Tunga penetrans; and Tylenchida, e.g., Melodidogyne incognita, Pratylenchus penetrans.

The following examples are presented by way of illustration, not by way of limitation.

EXAMPLES

Example 1
Bacterial Strains and Plasmids

Bacillus thuringiensis subsp. tenebrionis strains NB125 and NB176 as noted above have been deposited with the Deutsche Saniung von Mikroorganismen und Zelkylturen GmbH with a designation of DSM 5526 and DSM 5480 respectively, Bacillus thuringiensis subsp. kurstaki EMCC0086 has been deposited with the NRRL and assigned accession number NRRL B-21147; and Bacillus thuringiensis subsp. aizawai EMCC0087 has been deposited with the NRRL and assigned accession number NRRL B-21148. Bacillus thuringiensis subsp. kurstaki 4D7 (cry⁻ HD1) are obtained from the Bacillus Genetic Stock Center at Ohio State University. Escherichia coli GM48 (Yanish-Perron et al., 1985, Gene 33:103–119; dam⁻ dcm⁻) is obtained from the laboratory of Dr. Chester Price, University of Califormia at Davis. E. coli ER1648 (Raleigh et al., 1989, Genetics 122:279–296) and E. coli GM272 (Raleigh et al., 1988, Nucl. Acids Res. 16:1563–1575; dam⁻ dcm⁻ hsd⁻) are obtained from New England Biolabs. Integrational plasmid pCP115 (Price et al., 1983, Proc. Natl. Acad. Sci. U.S.A. 80:4074–4078 and Price and Doi, 1985, Mol. Gen. Genet. 201:88–95) is obtained from Dr. Chester Price. Plasmids pUC118 (Vieira and Messing, 1987, Methods Enzymol. 153:3–11) and pBR322 may be obtained through commercial sources. Plasmid pMI1101D is disclosed in Youngman et al., (1984, Plasmid 12:1–9). Plasmids pE194$^{ts}$ and pPL1975 are disclosed in WO 91/09129.

Example 2
Preparation of Genomic DNA

DNA from either Bacillus thuringiensis subsp. tenebrionis NB125, Bacillus thuringiensis subsp. tenebrionis NB176, or Bacillus thuringiensis subsp. aizawai EMCC0087 is prepared by inoculating 2 ml LB (Luria-Bertani broth) in a 15×1.5 cm screw-capped test tube with a Bacillus thuringiensis colony. After overnight incubation at 37° C. without shaking, the entire tube contents are transferred to a 1 L flask containing 250 ml LB and grown for 6 hours at 37° C. with shaking at 300 rpm. Flask contents are harvested at 8000 rpm in a GSA rotor, and the resulting pellet is resuspended in 20 ml TE buffer (10 mM Tris, pH 7.9, 1 mM EDTA) in a 25 ml Corex centrifuge tube. Approximately 20 mg solid lysozyme is added and the tube contents are mixed by gentle inversion. After a 10 minute incubation at 37° C., 1 ml 0.5 M EDTA and 0.5 ml 2 M Tris, pH 7.9 are added. The tube contents are again mixed by gentle inversion and allowed to incubate for an additional 15 minutes. Subsequently, 200 μl RNase A (10 mg/ml) is added, followed by a 15 minute incubation at 37° C. and addition of 2.3 ml of 10% SDS. Proteinase K (2 mg) is added, and the tube contents are incubated for 2 hrs. at 50° C., split into two Corex tubes, and extracted at least two times with phenol and two times with phenol/chloroform. Genomic DNA is precipitated with 1/10 volume of sodium acetate and 2.5 volumes of 95% ethanol, and resuspended in approximately 5 ml of TE buffer.

Example 3
Construction of Plasmid pET105

A size-selected library of Bacillus thuringiensis subsp. tenebrionis NB176 DNA fragments is created by digestion of genomic DNA with HindIII, gel electrophoresis, excision of the 3–5 kb fragments, and release from the agarose by digestion with agarase (New England BioLabs). After ligation of the fragments into pUC118 and transformation into E. coli strain ER1648, the 3.0 and 4.0 kb HindIII fragments bearing the cryIIIA gene are cloned by colony blot hybridization as previously described (Sambrook et al., 1989, Molecular Cloning, A Laboratory Manual, Cold Spring Harbor, N.Y.), using a "cryIIIA" probe corresponding to nucleotides 1493 to 1811 of the cryIIIA gene (Donovan et al., 1988, Mol. Gen. Genet. 214:365–372)(SEQ ID NO:1). This probe (SEQ ID NO:1), is generated by polymerase chain reaction (PCR) amplification of the region corresponding to nucleotides 1493–1811 of the 3 kb HindIII fragment.

Figure 2:
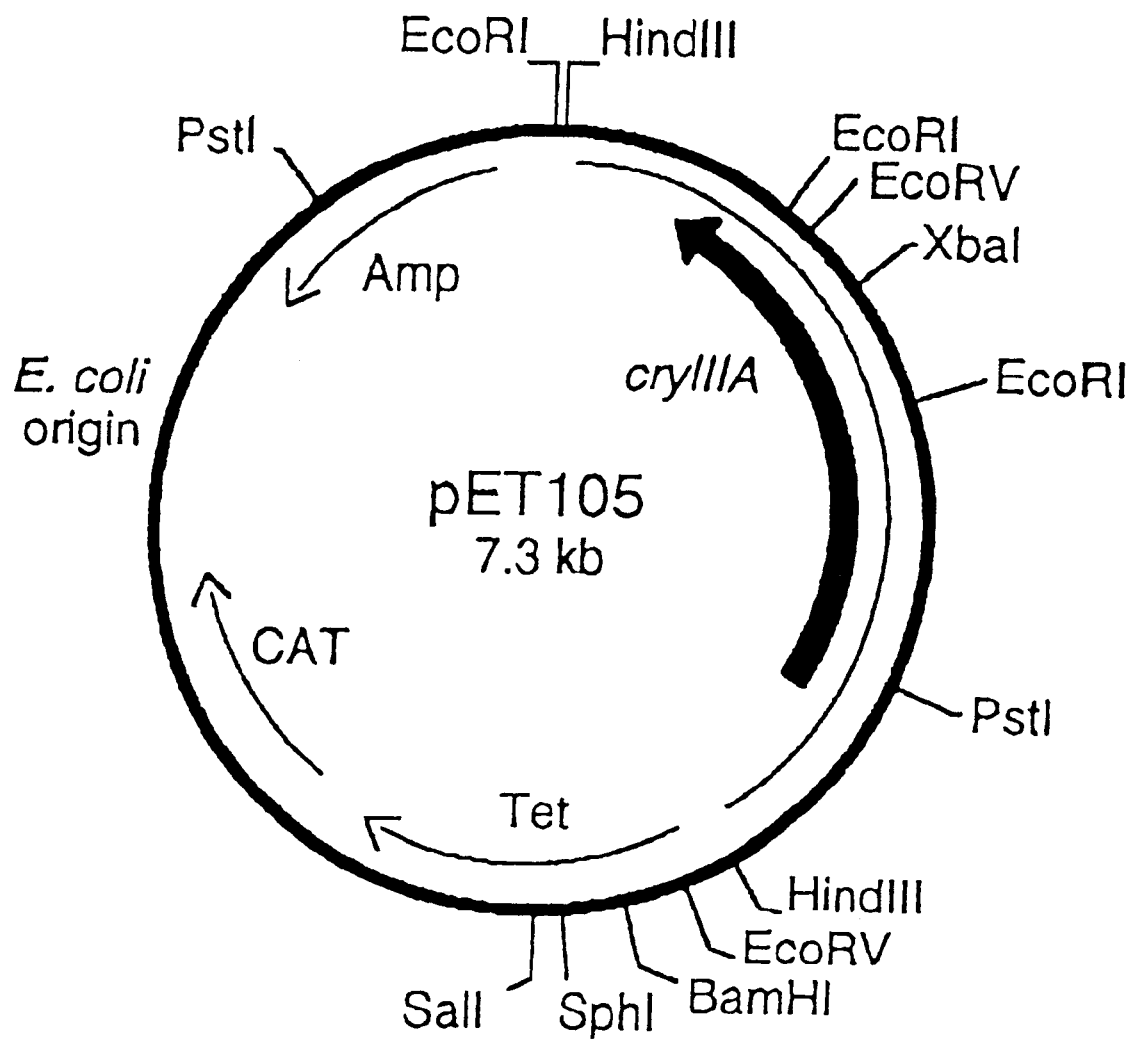
FIG. 2 shows a map of plasmid pET105.
Figure 3:
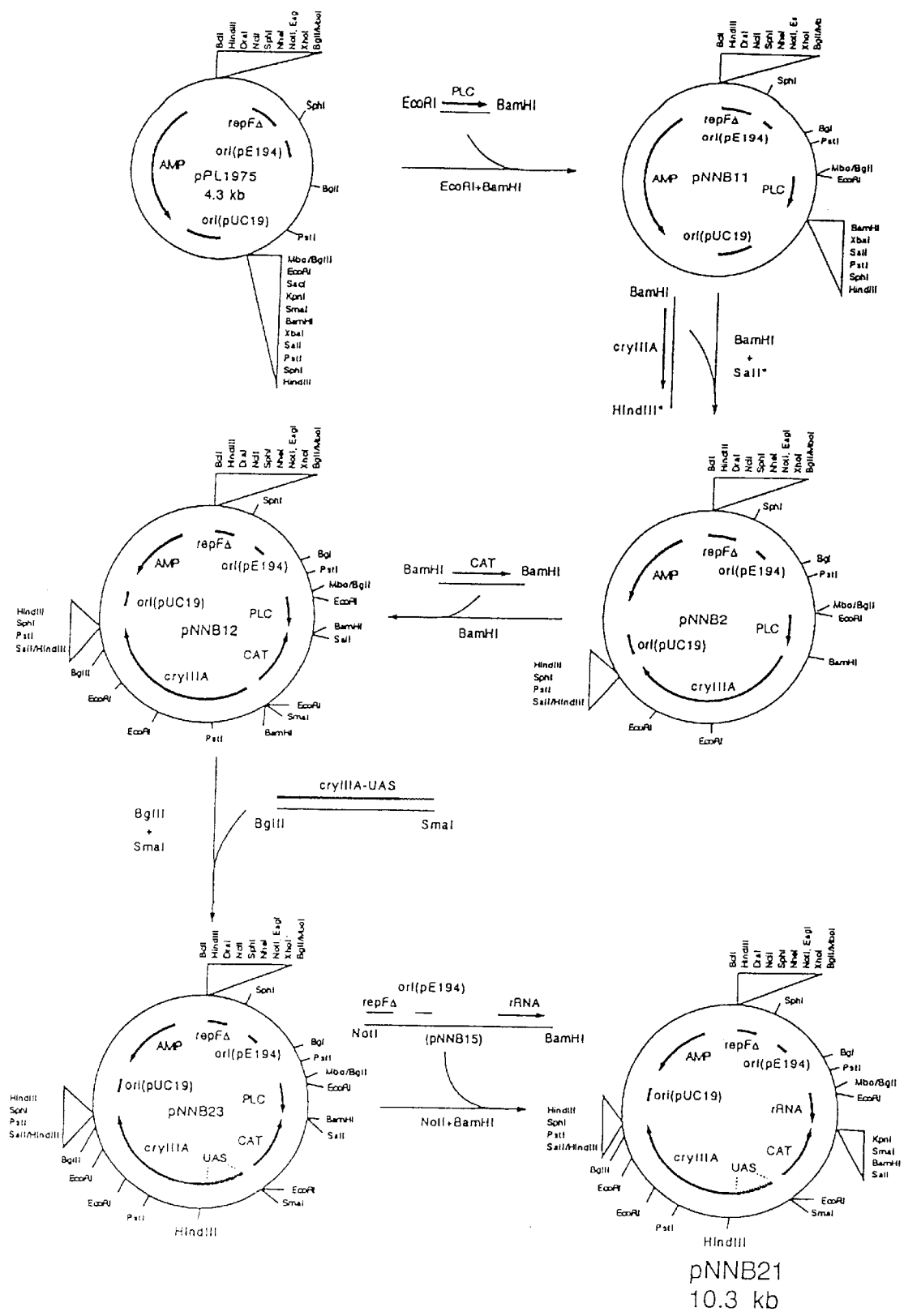
FIG. 3 shows the construction of plasmid pNNB21.
Figure 4:
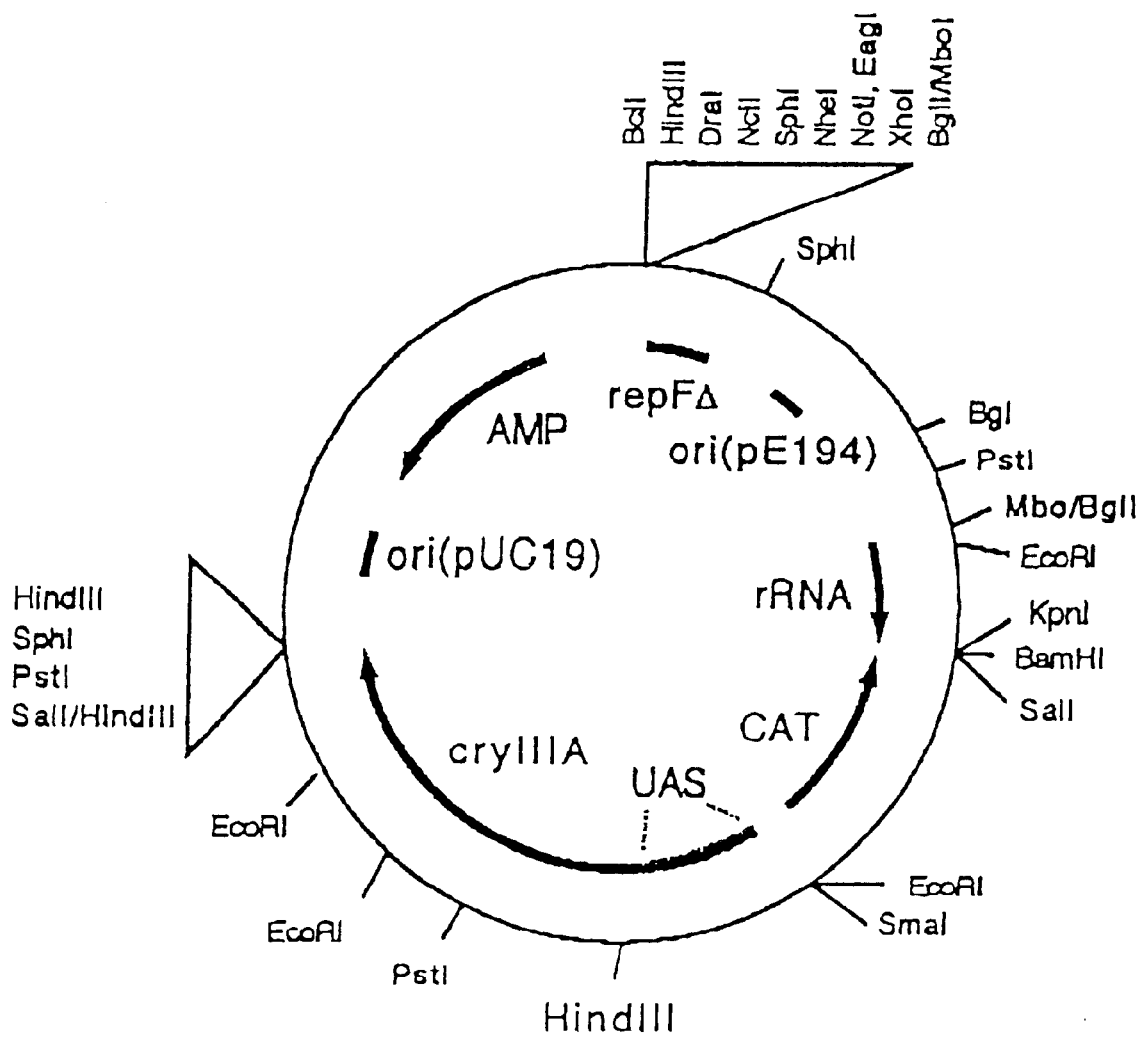
FIG. 4 shows a map of plasmid pNNB21.

Plasmid pET105 (see FIG. 2) is constructed by insertion of the 3.0 kb HindIII fragment cloned from Bacillus thuringiensis subsp. tenebrionis NB176 into the HindIII site of pCP115.

Example 4
Integration and Amplification of Plasmid pET105

E. coli cells are electroporated with a Bio-Rad Gene Pulser as described by the manufacturer. Bacillus thuringiensis NB125 cells are prepared for electroporation by the method of Macaluso and Mettus (1991, J. Bacteriol. 173:1353–1356). However, unlike their procedure, no electrical modifications are made to the Gene Pulser; instead, cells are placed in a 0.2 cm cuvette and electroporated at 800 ohms, 25 μF, and 1600 volts (8000 volts per cm). Plasmid DNA for electroporation is prepared in E. coli GM272 (dam⁻ dcm⁻ hsd⁻), which generally yields higher efficiencies for transformation of Bacillus thuringiensis than does plasmid DNA prepared from GM48 (dam⁻ dcm⁻). Colonies are selected on BHIG (Brain Heart Infusion plus 0.5% glycerol final concentration) containing 5 μg chloramphenicol per ml. The selected colonies are subsequently serially plated at 10, 20, and 40 μg chloramphenicol/ml.

Two integrants, EMCC0082 and EMCC0083, are selected based on crystal size as described in EXAMPLE 5, infra.

Example 5
Determination of Crystal Size of Bacillus thuringiensis subsp. tenebrionis NB125 cryIIIA Integrants EMCC0082 and EMCC0083

The crystal measurements are made by photographing spore/crystal preparations with a Zeiss Axioscope, and then printing the negatives at a final magnification of approximately 2000×. Measurements of the crystals in millimeters are made with a ruler, and then normalized to the average length of the spores in each photo to account for any differences in photo enlargement. Assuming that a mature endospore is approximately 1 μm in its longest diameter, then the crystals have the dimensions indicated in Table 1.

The results, shown in Table 1, infra, indicate that the largest face of the crystal of integrant EMCC0082 has more than 1.5 times the surface area of NB125 and the largest face of the crystal of the integrant EMCC0083 has more than twice the surface area of the NB125.

| | KH$_2$PO$_4$ | 1.77 g/L |
| | K$_2$HPO$_4$ | 4.53 g/L |

The pH of the medium is adjusted to 7.0 using 10 N NaOH.

After inoculation, shake flasks are incubated at 30° C. on a rotary shaker with 250 rpm shaking for 72 hours. The whole culture broths are stored at −70° C. until testing against Leptinotarsa texana.

Example 7
Bioassay of Crystal Delta-endotoxins from Bacillus thuringiensis subsp. tenebrionis NB125 cryIII Integrants EMCC0082 and EMCC0083 against Leptinotarsa texana The potencies of the Bacillus thuringiensis subsp. tenebrionis integrants, EMCC0082 and EMCC0083, are determined in bioassay against Leptinotarsa texana by comparison with a reference substance (BMB0020), which is assigned a potency of 20,000 units per gram of liquid. BMB0020 is a concentrated and stabilized formulation of a Bacillus thuringiensis subsp. tenebrionis strain NB176 culture.

Dilutions for a standard curve are made by weighing 120 mg of the reference substance, BMB0020, in a 50 ml centrifuge tube, and adding 0.1% Tween 20 in deionized water to bring the total weight to 10 g. Dilutions of this solution of 1:4, 1:6, 1:9, 1:14, 1:22, 1:33, and 1:49 are then made with appropriate volumes of the Tween 20 solution. Dilutions of the various integrant strains and control strains are made by weighing 320 mg from liquid cultures of the integrants and resuspending in 0.1% Tween 20 to a final weight of 10 g. Subsequent dilutions are performed as described for the reference substance.

Eggplant leaves sufficient for eight leaf discs are laid on a 12×24 inch piece of butcher paper so that the leaves are lined up along a center line of the paper. The highest dilution (1:49) of the reference substance is placed in the tube of a Devries Linear Track Sprayer and applied to the eggplant

TABLE 1

Crystal Dimensions of cryIIIA Integrants EMCC0082 and EMCC0083

| Sample | Crystal Length (μm) | Range (μm) | Crystal Width (μm) | Range (μm) | Surface Area of Large Face (μm$^2$) | Number Measured |
|---|---|---|---|---|---|---|
| EMCC0082 | 0.73 ± 0.25 | 0.35–1.23 | 0.58 ± 0.15 | 0.35–0.79 | 0.42 | 16 |
| EMCC0083 | 0.95 ± 0.27 | 0.51–1.27 | 0.66 ± 0.15 | 0.38–0.89 | 0.63 | 14 |
| NB125 | 0.50 ± 0.09 | 0.35–0.69 | 0.50 ± 0.09 | 0.34–0.69 | 0.25 | 18 |

Example 6
Cultivation of Bacillus thuringiensis subsp. tenebrionis NB125 cryIII Integrants EMCC0082 and EMCC0083

Subcultures of EMCC0082 and EMCC0083, maintained on Nutrent Broth Agar plates, are used to inoculate 250 ml baffled shake flasks containing 50 ml of medium with the following composition.

| Corn Steep liquor | 15 g/L |
| Maltrin-100 | 40 g/L |
| Potato Starch | 30 g/L | leaves with a hollow cone nozzle (droplet size of approx 150 μm) from a distance of 18" at a rate of approx 18 gallons per acre. Experimental controls consist of leaves sprayed with deionized water (0.1% Tween 20). The spraying regime is repeated for all of the other concentrations, and the spray track tube and nozzle are rinsed with 100 ml of 0.1% Tween 20 between samples.

After the foliage had dried, five early second instar Leptinotarsa texana larvae are placed in a one ounce cup. Eggplant leaves, sprayed side down, are placed on the rim of the cup containing the larvae. A lid is placed on top of the leaves and pressed downwards to cut the leaf.

Portions of the leaf extending beyond the lid are removed to prevent desiccation of the foliage inside of the cup. Eight replicates (cups) containing five larvae are made for each concentration.

Cups are then taped together, labelled, and placed in a holding room maintained at 29° C., 65% relative humidity, and a 16h: 8h light:dark photoperiod.

The number of dead larvae are recorded three days after treatment $LC_{50}$ values and potencies are calculated by parallel probit analysis. (Potency of sample in Btt units per g is [($LC_{50}$ of the standard BMB0020)/$CLC_{50}$ of sample)] (20,000 Btt units/g).

The results are shown in Table 2, infra. The potency of EMCC0083 is more than three times that of *Bacillus thuringiensis* subsp. *tenebrionis* strain NB125 and the potency of EMCC0082 is more than 6 times the potency of *Bacillus thutingiensis* subsp. *tenebrionis* strain NB125.

TABLE 2

Potency of cryIIIA Integrants of NB125 Against *Leptinotarsa texana*

| Sample | Bioassay (Btt units/gram) | LC50 (μg/ml) |
|---|---|---|
| EMCC0082 | 7069 | 2950 |
| EMCC0083 | 4024 | 5090 |
| NB125 | 1124 | 20230 |
| NB176 | 2059 | 7640 |

Example 8

Construction of Plasmid pNNB21

Plasmid pNNB21 is constructed in multiple steps as summarized in FIG. 5. The phospholipase C (plc) gene of *Bacillus thuringiensis* subsp. *kurstaki* 4D7 is PCR amplified using primers depicted in SEQ ID NO:2 and SEQ ID NO:3 containing BamHI sites. This fragment (~1400 bp) is subcloned and an 850 bp EcoRI-BamHI fragment containing the 3' half of the plc gene is cloned into pPL1975 to generate pNNB11. The 3.0 kb HindIII fragment harboring the cryIIIA gene (the HindIII site at the 5' end is deleted and replaced with a BamHI site) is next cloned into the BamHI-SalI site of pNNB15 to yield pNNB2. The HindIII and SalI sites are filled in with Klenow fragment. The 1.6 kb BamHI fragment from pMI1101D harboring the cat gene is then cloned into the BamHI site in the orientation shown to yield pNNB12. The 1.0 kb HindIII fragment containing the upstream activating sequence of the cryIIIA gene (UAS) is PCR amplified from *Bacillus thuringiensis* subsp. *tenebrionis* strain 225 NB125 with primers shown in SEQ ID NO:4 and SEQ ID NO:5 to yield a SmaI site at the 5' end and a HindIII site at the 3' end of the fragment and subsequently cloned into Stratagene's Bluescript KS+ vector. The 3.0 kb HindIII fragment harboring the cryIIIA gene is then cloned into the unique HindIII site of this plasmid to reconstruct the 4.0 kb UAS-cryIIIA gene fragment. The SmaI-BglII fragment from this plasmid is then used to replace the corresponding SmaI-BglII segment of pNNB12 to yield pNNB23.

The first 450 bp of the 16S rRNA gene of *Bacillus thuringiensis* subsp. *kurstaki* 4D7 is PCR amplified with primers depicted in SEQ ID NO:6 and SEQ ID NO:7 to yield an EcoRI site at the 5' end and a KpnI site at the 3' end of the fragment. Once amplified, the fragment is cloned into the EcoRI-KpnI site of pPL1975 to yield pNNB15. Finally, the NotI-BamHI fragment from this plasmid (harboring the rRNA segment) is used to replace the NotI-BamHI fragment of pNNB23 (harboring the plc segment) to generate pNNB21 (see FIG. 4).

Example 9

Integration and Amplification of Plasmid pNNB21

*Bacillus thuringiensis* subsp. *tenebrionis* strain NB125 is incubated at 42° C. to cure the strain of its native plasmid containing the cryIIIA gene. Total DNA is isolated from one colony and PCR analysis indicates that the strain has lost the cryIIIA gene.

The cured *Bacillus thuringiensis* subsp. *tenebrionis* NB125 strain is then transformed with $pE194^{ts}$ by electroporation as described in EXAMPLE 4 selecting for erythromycin resistance ($ery^r$) at 30° C. One colony is selected, NB125C/$pE194^{ts}$, and this strain is then transformed with pNNB21 (see FIG. 4), selecting for chloramphenicol resistance ($cm^r$) at 30° C. Since pNNB21 encodes a defective Rep protein, the plasmid can only replicate if supplied with Rep protein in trans from $pE194^{ts}$. One ($cm^r$) colony is selected and the strain is patched onto erythromycin plates to check for $ery^r$ at 30° C. A $cm^r$ and $ery^r$ strain has both plasmids, $pE194^{ts}$ and pNNB21. This strain is then grown at 37° C. and plated onto media containing 10 μg/ml chloramphenicol at 37° C. One $cm^r$, $ery^s$ colony is selected. Since $pE194^{ts}$ does not replicate at 37° C., pNNB21 is forced by maintaining selection to integrate by a homologous crossover event at a 16S rRNA locus in the chromosome. This strain is designated EMCC0115.

Tandem repeats (amplification) of pNNB21 in the chromosome are selected by picking single colonies that grow in the presence of higher chloramphenicol concentrations. Single colonies that grow in the presence of 60 μg/ml are obtained.

Analysis of isolated chromosomal DNA from EMCC0115 indicates a copy number of approximately 10–30 for the amplified DNA.

One integrant, EMCC0115, is selected based on crystal size as described in EXAMPLE 10, infra.

Example 10

Determination of Crystal Size of *Bacillus thuringiensis* subsp. *tenebrionis* NB125 cryIIIA Integrant EMCC0115

The size of the crystal is determined as described in EXAMPLE 5.

The results, shown in Table 3, infra, indicate that the largest face of the crystal of integrant EMCC0115 has more than 2.0 times the surface area of the crystal of *Bacillus thuringiensis* subsp. *tenebrionis* NB125.

TABLE 3

Crystal Dimensions of cryIIIA Integrant EMCC0115

| Sample | Crystal Length (μm) | Range (μm) | Crystal Width (μm) | Range (μm) | Surface Area of Large Face ($μm^2$) | Number Measured |
|---|---|---|---|---|---|---|
| EMCC0115 | 1.29 ± 0.47 | 0.63–2.22 | 0.41 ± 0.13 | 0.47–0.95 | 0.52 | 17 |
| NB125 | 0.50 ± 0.09 | 0.35–0.69 | 0.50 ± 0.09 | 0.34–0.69 | 0.25 | 18 |

Example 11
Cultivation of *Bacillus thuringiensis* subsp. *tenebrionis* NB125 cryIIIA Integrant EMCC0115

*Bacillus thuringiensis* subsp. *tenebrionis* NB125 cryIIIA integrant EMCC0115 is cultivated as described in EXAMPLE 6.

Example 12
Bioassay of Crystal Delta-endotoxin from *Bacillus thuringiensis* subsp. *tenebrionis* NB176 cryIIIA Integrant-EMCC0115 against *Leptinotarsa texana*

The potency of the *Bacillus thuringiensis* subsp. *tenebrionis* cryIIIA integrant EMCC0115 is determined in bioassay against *Leptinotarsa texana* as described in EXAMPLE 7.

The results are shown in Table 4, infra. The potency of EMCC0115 is similar to that of *Bacillus thuringiensis* subsp. *tenebrionis* NB176 which produces a crystal delta-endotoxin with a larger crystal size and greater pesticidal activity as compared to a corresponding parental strain (Gurtler and Petersen, 1994, U.S. Pat. No. 5,279,962).

TABLE 4

Potency of cryIIIA Integrant EMCC0115 to *Leptinotarsa texana*

| Strain | LTU/g | Std. Dev. |
|---|---|---|
| EMCC0115 | 4,747 | 1,076 |
| NB176 | 5,443 | 1,573 |

Example 13
Construction of Plasmid pET235

A size-selected library of *Bacillus thuringiensis* subsp. *aizawai* EMCC0087 DNA fragments is created by digestion of genomic DNA with EcoRI, gel electrophoresis, excision of fragments 6 kb and larger, and release from the agarose by electroelution. After ligation of the fragments into the EcoRI site of pBR322 and transformation into *E. coli* strain XL-1 Blue MRF' (Stratagene Cloning Systems; Jerpseth et al., 1992, Strategies 5[3]:81), the 8-kb EcoRI fragment bearing the cryIC gene is cloned by colony blot hybridization as previously described (Sambrook et al., 1989, *Molecular Cloning, A Laboratory Manual,* Cold Spring Harbor, N.Y.), probing with a DNA fragment corresponding to nucleotides 869 to 1175 of the cryIC gene (Honée et al., 1988, Nucleic Acids Research 16:6240) with the addition of four nucleotides (CGGG) to the 5' end to create a functional BamH1 site. This probe SEQ ID NO:10, is generated by PCR amplification of *Bacillus thuringiensis* subsp. *aizawai* EMCC0087 genomic DNA.

Figure 5:
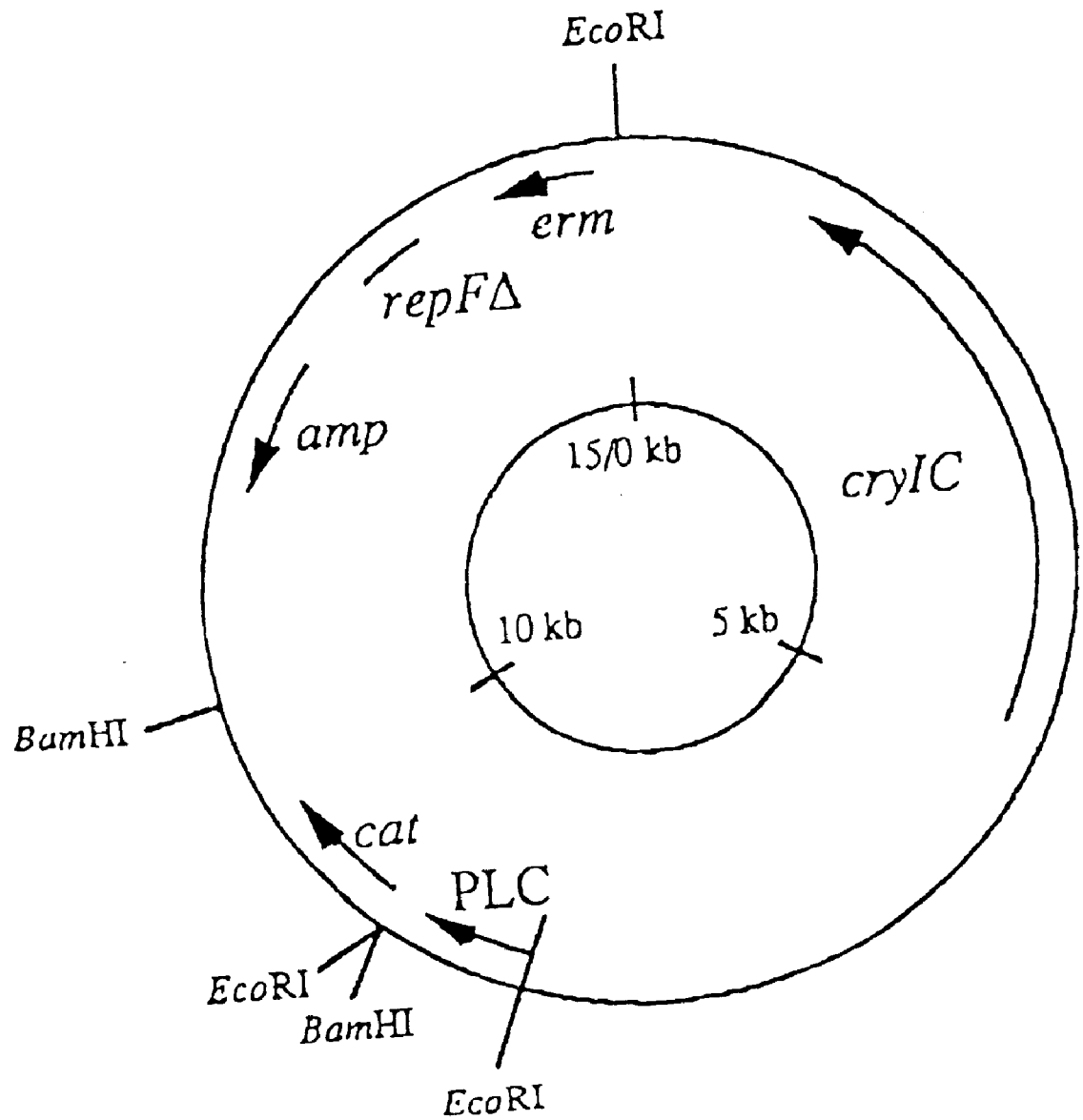
FIG. 5 shows a map of plasmid pET235

Plasmid pET231 is constructed by insertion of the 8-kb EcoRI fragment into the EcoRI site of pNNB11 (see EXAMPLE 8, supra). Plasmid pET235 (see FIG. 5) is constructed by insertion of the cat-bearing 1.5-kb BamHI fragment of pMI1101D into the BamHI site of pET231.

Example 14
Integration and Amplification of Plasmid pET235

Cells are electroporated as described in Example 4. *Bacillus thuringiensis* subsp. *aizawai* EMCC0087 is transformed with pE194$^{ts}$, and colonies are selected on LB plates containing 5 µg erythromycin per ml. *Bacillus thuringiensis* subsp. *aizawai* EMCC0087 bearing helper plasmid pE194$^{ts}$ is transformed with pET235, and colonies are selected on LB plates containing 10 µg chloramphenicol per ml. Integrants are formed by incubating the transformants at 37° C. to cure them of pE194$^{ts}$. Erydiromycin sensitive colonies are subsquently serially plated at 30 and 60 µg choramphenicol per ml.

One integrant, EMCC0116, is selected based on crystal size as described in EXAMPLE 19, infra.

Example 15
Determination of Crystal Size of *Bacillus thuringiensis* subsp. *aizawai* EMCC0087 cryIC Integrant EMCC0116

The size of the crystal is determined as described in EXAMPLE 5.

The results, shown in Table 5, infra, indicate that the volume of the crystal of integrant EMCC0116 is more than 1.2 times the volume of the crystal of *Bacillus thuringiensis* subsp. *aizawai*. EMCC0087.

TABLE 5

Crystal Dimensions of cryIC Integrant EMCC0116

| Sample | Crystal Length (µm) | Range (µm) | Crystal Width (µm) | Range (µm) | Surface Volume (µm³) | Number Measured |
|---|---|---|---|---|---|---|
| EMCC0116 | 1.1 ± 0.16 | 0.74–1.3 | 0.58 ± 0.07 | 0.46–0.71 | 0.12 ± 0.05 | 20 |
| EMCC0087 | 0.99 ± 0.18 | 0.66–1.4 | 0.54 ± 0.08 | 0.42–0.66 | 0.10 ± 0.05 | 18 |

Example 16
Cultivation of *Bacillus thuringiensis* subsp. *aizawai* EMCC0087 crvIC Integrant EMCC0116

A subculture of *Bacillus thuringiensis* subsp. *aizawai* EMCC0087cryIC integrant EMCC0116, maintained as a 40% glycerol stock stored at–80° C., is used to inoculate 250 ml baffled shake flasks containing 50 ml of P/Y medium, having the following composition.

| | |
|---|---|
| Citric acid | 1.0 g/l |
| KH$_2$PO$_4$ | 1.3 g/l |
| CaCl$_2$.H$_2$O | 0.33 g/l |
| MgSO$_4$.7H$_2$O | 0.67 g/l |
| Maltrin-100 | 20 g/l |
| Yeast Extract | 10 g/l |

| | |
|---|---|
| Peptone | 15.3 g/l |
| Trace metals | 0.3 ml/l |

The pH of the medium is adjusted to 7.0 using 10 N NaOH.

After inoculation, shake flasks are incubated at 30° C. on a rotary shaker with 250-rpm shaking for 72 hours. The whole cultures are stabilized by addition of 10 mg potassium sorbate, 3 mg sodium benzoate, and 0.5 mg methyl paraben per ml of culture and adjustment to pH 4.5 with 30% $H_3PO_4$, and are stored at 5° C.

Example 17

Bioassay of Crystal Delta-endotoxins from *Bacillus thuringiensis* subsp. *aizawai* EMCC0087cryIC Integrant EMCC0116 against *Spodoptera exigua*

The potency of the *Bacillus thuringiensis* subsp. *aizawai* EMCC0087cryIC integrant EMCC0115 is determined by diet incorporation bioassay as described in EXAMPLE 17 except using third instar *Spodoptera exigua*.

The results are shown in Table 8, infra. The potency of EMCC0116 is approximately 3 times that of *Bacillus thuringiensis* subsp. *aizawai*. EMCC0087.

TABLE 6

Potency of cryIC Integrant EMCC0116 against *Spodoptera exigua*

| Sample | LC50 | LC90 | Slope | CV | SU |
|---|---|---|---|---|---|
| EMCC0087 | 3127 | 16922 | 2.1 | 10.2 | 750 |
| EMCC0116 | 1177 | 3918 | 2.5 | 10.3 | 1770 |

DEPOSIT OF MICROORGANISMS

The following strains of *Bacillus thuringiensis* have been deposited in the Agricultural Research Service Patent Culture Collection, Northern Regional Research Laboratory (NRRL), 1815 University Street, Peoria, Ill., 61604, USA.

| Strain | Accession Number | Deposit Date |
|---|---|---|
| EMCC0082 | NRRL B-21106 | May 26, 1993 |
| EMCC0083 | NRRL B-21107 | May 26, 1993 |
| EMCC0115 | NRRL B-21286 | June 23, 1994 |
| EMCC0116 | NRRL B-21287 | June 23, 1994 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

Further, the subject culture deposit will be stored and made available to the public in accordance with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for obtaining an integrant of *Bacillus thuringiensis* which has greater pesticidal activity than a corresponding parental strain by producing a larger quantity of a crystal delta-endotoxin as compared to said corresponding parental strain wherein the crystal delta-endotoxin produced by the integrant *Bacillus thuringiensis* has an activity directed towards the same pest as the crystal delta-endotoxin produced by the corresponding parental strain comprising (a) introducing into a cell of a parental strain a DNA construct lacking a *Bacillus thuringiensis* origin of replication comprising (i) a DNA sequence encoding a delta-endotoxin, wherein said delta-endotoxin is the same delta-endotoxin as the parental strain delta-endotoxin, (ii) a DNA sequence which is homologous with a region of the genome of said cell; and (iii) a selectable marker; and (b) integrating the introduced DNA construct of step (a) into the genome of the cell of said parental strain by homologous recombination in the presence of a selecting agent to obtain an integrant.

2. The method according to claim 1 in which the delta-endotoxin produced has a larger crystal size as compared to the crystal delta-endotoxin produced by the parental strain.

3. The method according to claim 1 wherein the parental strain of step (a) is a wild-type strain.

4. The method according to claim 1 wherein the DNA sequence encoding the delta-endotoxin is selected from the group consisting of a cryI gene, cryII gene, cryIII gene, cryIV gene, cryV gene, and a cryVI gene.

5. The method according to claim 1 wherein the DNA sequence encoding the delta-endotoxin comprises a cryIIIA gene.

6. The method according to claim 1 wherein the integrant is selected from the group consisting of an integrant which has all of the identifying characteristics of strain EMCC0082, deposited with the NRRL, having an accession number of NRRL B-21106 and an integrant which has all of the identifying characteristics of strain EMCC0083, deposited with the NRRL, having an accession number of NRRL B-21107.

7. The method according to claim 1 wherein the DNA sequence encoding the delta-endotoxin is obtained from a *Bacillus thuringiensis* strain selected from the group consisting of *Bacillus thuringiensis* subsp. *kurstaki, Bacillus thuringiensis* subsp. *aizawai, Bacillus thuringiensis* subsp. *galleriae, Bacillus thuringiensis* subsp. *entomocidus, Bacillus thuringiensis* subsp. *tenebrionis, Bacillus thuringiensis* subsp. *thuringiensis, Bacillus thuringiensis* subsp. *alesti, Bacillus thuringiensis* subsp. *canadiensis, Bacillus thuringiensis* subsp. *darmstadiensis, Bacillus thuringiensis* subsp. *dendrolimus, Bacillus thuringiensis* subsp. *finitimus, Bacillus thuringiensis* subsp. *kenyae, Bacillus thuringiensis* subsp. *morrisoni, Bacillus thuringiensis* subsp. *subtoxicus, Bacillus thuringiensis* subsp. *toumanoffi*, and *Bacillus thuringiensis* subsp. *israelensis*.

8. The method according to claim 1 wherein the DNA sequence encoding the delta-endotoxin is obtained from a *Bacillus thuringiensis* subsp. *tenebrionis* strain.

9. The method according to claim 1 wherein the DNA sequence encoding the delta-endotoxin is obtained from a mutant or variant *Bacillus thuringiensis* subsp. *tenebrionis* strain which produces a high amount of delta-endotoxin as compared to a corresponding wild-type strain.

10. The method according to claim 1 wherein the selectable marker is a DNA sequence encoding antibiotic resistance.

11. The method according to claim 1 wherein said method further comprises amplifying the integrated DNA sequence by culturing the integrant of step (b) in the presence of increasing amounts of selecting agent.

12. A method for obtaining an integrant of *Bacillus thuringiensis* which has greater pesticidal activity than a corresponding parental strain by producing a larger quantity of a crystal delta-endotoxin as compared to said corresponding parental strain wherein the crystal delta-endotoxin produced by the integrant *Bacillus thuringiensis* has an activity directed towards the same pest as the crystal delta-endotoxin produced by the corresponding parental strain comprising (a) introducing into a cell of a parental strain (i) a first DNA vector comprising a first origin of replication and at least one functional gene encoding at least one factor required for plasmid replication from said first origin of replication, and (ii) a second DNA vector comprising a second origin of replication and a selectable marker but lacking a functional gene or portion thereof encoding a factor required for plasmid replication from the second origin of replication, as well as a DNA sequence encoding a *Bacillus thuringiensis* delta-endotoxin, and a DNA sequence that is homologous with a region of the genome of said cell, and (b) culturing the cell of step (a) under selective conditions leading to integration of said second DNA vector into the genome of the cell of said parental strain by homologous recombination and loss of the first DNA vector.

13. The method according to claim 12 wherein the parental strain of step (a) is a wild-type strain.

14. The method according to claim 12 wherein the DNA sequence encoding the delta-endotoxin is selected from the group consisting of a cryI gene, cryII gene, cryIII gene, cryIV gene, cryV gene, and cryVI gene.

15. The method according to claim 12 wherein the DNA sequence encoding a delta-endotoxin is selected from the group consisting of a cryIIIA gene and a cryIC gene.

16. The method according to claim 12 wherein the integrant is selected from the group consisting of an integrant which has all of the identifying characteristics of strain EMCC0115, deposited with the NRRL, having an accession number of NRRL B-21286 and an integrant which has all of the identifying characteristics of strain EMCC00116, deposited with the NRRL, having an accession number of NRRL B-21287.

17. The method according to claim 12 wherein the DNA sequence encoding the delta-endotoxin is obtained from a *Bacillus thuringiensis* strain selected from the group consisting of *Bacillus thuringiensis* subsp. *kurstaki, Bacillus thuringiensis* subsp. *aizawai, Bacillus thuringiensis* subsp.

*galleriae, Bacillus thuringiensis* subsp. *entomocidus, Bacillus thuringiensis* subsp. *tenebrionis, Bacillus thuringiensis* subsp. *thuringiensis, Bacillus thuringiensis* subsp. *alesti, Bacillus thuringiensis* subsp. *canadiensis, Bacillus thuringiensis* subsp. *darmstadiensis, Bacillus thuringiensis* subsp. *dendrolimus, Bacillus thuringiensis* subsp. *finitimus, Bacillus thuringiensis* subsp. *kenyae, Bacillus thuringiensis* subsp. *morrisoni, Bacillus thuringiensis* subsp. *subtoxicus, Bacillus thuringiensis* subsp. *toumanoffi,* and *Bacillus thuringiensis* subsp. *israelensis.*

18. The method according to claim 12 wherein the DNA sequence encoding the delta-endotoxin is obtained from a *Bacillus thuringiensis* strain selected from the group consisting of *Bacillus thuringiensis* subsp. *aizawai,* and *Bacillus thuringiensis* subsp. *tenebrionis.*

19. The method according to claim 12 wherein the first DNA vector further comprises a functional gene encoding the replication factor associated with the second origin of replication.

20. The method according to claim 12 wherein the selectable marker from the second DNA vector is a DNA sequence encoding antibiotic resistance.

21. The method according to claim 12 in which the first DNA vector further comprises a selectable marker and in which said selectable marker differs from the selectable marker in the second DNA vector.

22. The method according the claim 12, wherein the first DNA vector comprises a first origin of replication from a single-strand DNA plasmid and a functional rep gene, and wherein the second DNA vector comprises a second origin of replication from a single-strand DNA plasmid but lacking a functional rep gene, a DNA sequence encoding a *Bacillus thuringiensis* delta-endotoxin, and a DNA sequence that is homologous with a region of the genome of said parental strain.

23. The method according to claim 12 wherein said method further comprises amplifying the integrated DNA sequence by culturing the integrant of step (b) in the presence of increasing amounts of a selecting agent.

24. The method according to claim 22 wherein the cell in step (b) is incubated at about 37° C.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 319 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

GTCGGAGTCA ACAACCTTAG GGGCTATGGA ACAACCTTCT CTAATATAGA AAATTATATT    60

CGAAAACCAC ATCTATTTGA CTATCTGCAT AGAATTCAAT TTCACACGCG GTTCCAACC    120

GGATATTATG GAAATGACTC TTTCAATTAT TGGTCCGGTA ATTATGTTTC AACTAGACC    180

AGCATAGGAT CAAATGATAT AATCACATCT CCATTCTATG GAAATAAATC CAGTGAACC    240

GTACAAAATT TAGAATTTAA TGGAGAAAAA GTCTATAGAG CCGTAGCAAA TACAAATCT    300

GCGGTCTGGC CGTCCGCTG                                                319

(2) INFORMATION FOR SEQ ID NO: 2:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 2:

TTGGATCCAG GGAAATATTA TTTATACGTC TATAAATAT                            39

(2) INFORMATION FOR SEQ ID NO: 3:

(i) SEQUENCE CHARACTERISTICS:
            (A) LENGTH: 74 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 3:

CCCCTTTAAC AACATAGACG ACAATGACTT GCAACTTAAT TGGATCCGAA TAAAAAATCA    60

TGTGGACTTC ATAG                                                      74

(2) INFORMATION FOR SEQ ID NO: 4:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 4:

GAGACCCGGG AGCTTTCAGT GAAGTACGTG                                     30

(2) INFORMATION FOR SEQ ID NO: 5:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 5:

GGGGCGTTAC AATTCAAAG                                                 19

(2) INFORMATION FOR SEQ ID NO: 6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

GGGGAATTCT TATTGGAGAG TTTGATCCT                              29

(2) INFORMATION FOR SEQ ID NO: 7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

CCTGGTACCG TTTTACGACC CGAAAGCCT                              29

(2) INFORMATION FOR SEQ ID NO: 8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

CGGGATCCTG GGTCAAAAAT TGATATTTAG TAAAATTAG                   39

(2) INFORMATION FOR SEQ ID NO: 9:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CCTGTCGACT AGAAAATAAC ATAGTAAAAC GGACATCACT CCG              43

(2) INFORMATION FOR SEQ ID NO: 10:

(i) SEQUENCE CHARACTERISTICS:
        (A) LENGTH: 311 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CGGGATCCAC AGTTACAGTC TGTAGCTCAA TTACCTACTT TTAACGTTAT GGAGAGCAGC    60

CGAATTAGAA ATCCTCATTT ATTTGATATA TTGAATAATC TTACAATCTT TACGGATTG    120

TTTAGTGTTG GACGCAATTT TTATTGGGGA GGACATCGAG TAATATCTAG CCTTATAGG    180

GGTGGTAACA TAACATCTCC TATATATGGA AGAGAGGCGA ACCAGGAGCC TCCAAGATC    240

```
TTTACTTTTA ATGGACCGGT ATTTAGGACT TTATCAAATC CTACTTTACG ATTATTACA        300

CAACCTTGGC C                                                            311
```